(12) United States Patent
Joskowicz et al.

(10) Patent No.: US 11,109,822 B2
(45) Date of Patent: Sep. 7, 2021

(54) METHOD OF NEEDLE LOCALIZATION VIA PARTIAL COMPUTERIZED TOMOGRAPHIC SCANNING AND SYSTEM THEREOF

(71) Applicant: Yissum Research Development Company of the Hebrew University of Jerusalem Ltd, Jerusalem (IL)

(72) Inventors: Leo Joskowicz, Jerusalem (IL); Guy Medan, Jerusalem (IL)

(73) Assignee: YISSUM RESEARCH DEVELOPMENT COMPANY OF THE HEBREW UNIVERSITY OF JERUSALEM LTD, Jerusalem (IL)

(*) Notice: Subject to any disclaimer, the term of this patent is extended or adjusted under 35 U.S.C. 154(b) by 205 days.

(21) Appl. No.: 16/545,811

(22) Filed: Aug. 20, 2019

(65) Prior Publication Data
US 2020/0054295 A1    Feb. 20, 2020

Related U.S. Application Data

(60) Provisional application No. 62/719,850, filed on Aug. 20, 2018.

(51) Int. Cl.
*A61B 6/12* (2006.01)
*A61B 6/00* (2006.01)
(Continued)

(52) U.S. Cl.
CPC ............. *A61B 6/12* (2013.01); *A61B 6/032* (2013.01); *A61B 6/5235* (2013.01); *G06F 17/16* (2013.01);
(Continued)

(58) Field of Classification Search
CPC ......... A61B 6/12; A61B 6/5235; A61B 6/032; A61B 2090/3762; A61B 2090/3937;
(Continued)

(56) References Cited

U.S. PATENT DOCUMENTS

| 2012/0308102 A1* | 12/2012 | Pack | G06T 11/006 |
| | | | 382/131 |
| 2016/0223698 A1* | 8/2016 | Wang | G01V 1/364 |
| 2016/0335785 A1* | 11/2016 | Joskowicz | G06T 11/005 |

OTHER PUBLICATIONS

Medan, Guy, Shamul, N, Joskowicz, L "Sparse 3D Radon Space Rigid Registration of CT Scans: Method and Validation Study" IEEE Transactions on Medical Imaging (Year: 2017).*

* cited by examiner

*Primary Examiner* — Kim Y Vu
*Assistant Examiner* — Molly Delaney
(74) *Attorney, Agent, or Firm* — Browdy and Neimark, PLLC

(57) ABSTRACT

There is provided a method of locating a tip of a metallic instrument inserted in a body, utilizing a baseline sinogram comprising projections in N exposure directions and derived from a prior computerized tomography (CT) scanning of the body, the method comprising: performing three-dimensional Radon space registration of a sparse repeat sinogram to the baseline sinogram, the repeat CT scanning having the metallic instrument inserted into the body, the metallic instrument having an attached marker located at a known distance from the instrument tip; subtracting the baseline sinogram from the repeat sinogram in accordance with the registration parameters to obtain projection difference images; and using the projection difference images and the known distance of the attached marker from the metallic instrument tip to determine a three-dimensional location of the metallic instrument tip.

20 Claims, 11 Drawing Sheets

(51) Int. Cl.
    *A61B 6/03*         (2006.01)
    *G06T 7/30*         (2017.01)
    *G06F 17/16*       (2006.01)
    *G06T 7/254*       (2017.01)

(52) U.S. Cl.
    CPC ................ *G06T 7/254* (2017.01); *G06T 7/30* (2017.01); *G06T 2207/10081* (2013.01); *G06T 2207/20224* (2013.01); *G06T 2207/30241* (2013.01)

(58) Field of Classification Search
    CPC ...... A61B 2034/2065; A61B 2034/102; A61B 34/20; G06T 7/30; G06T 7/254; G06T 2207/30241; G06T 2207/10081; G06T 2207/20224; G06T 2207/30204; G06T 2207/30021; G06T 7/74; G06F 17/16
    See application file for complete search history.

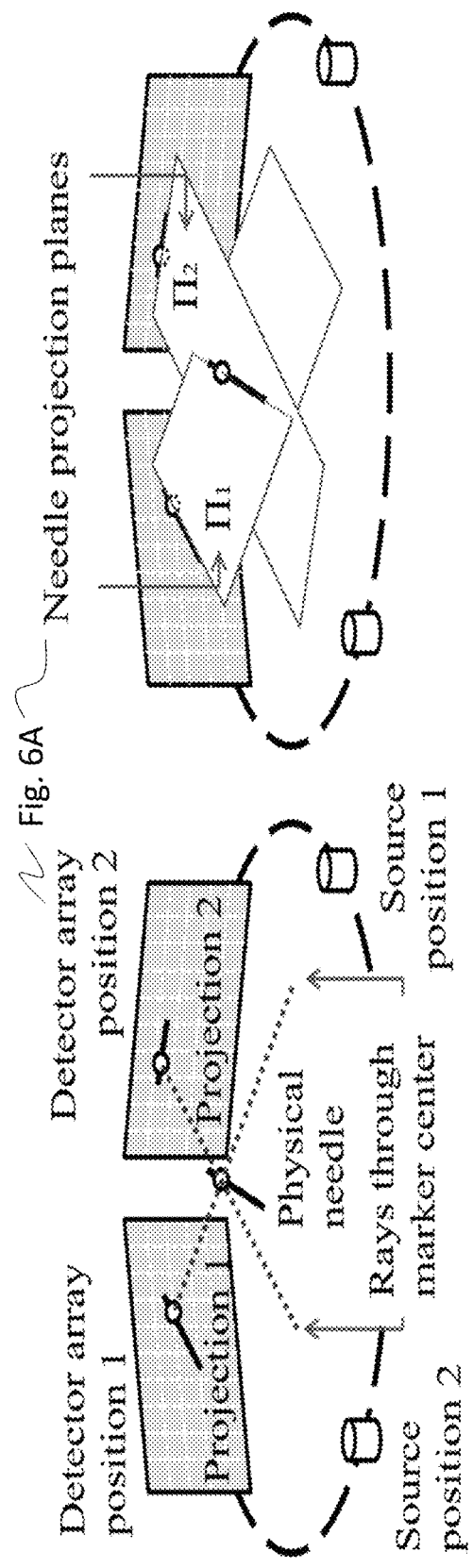
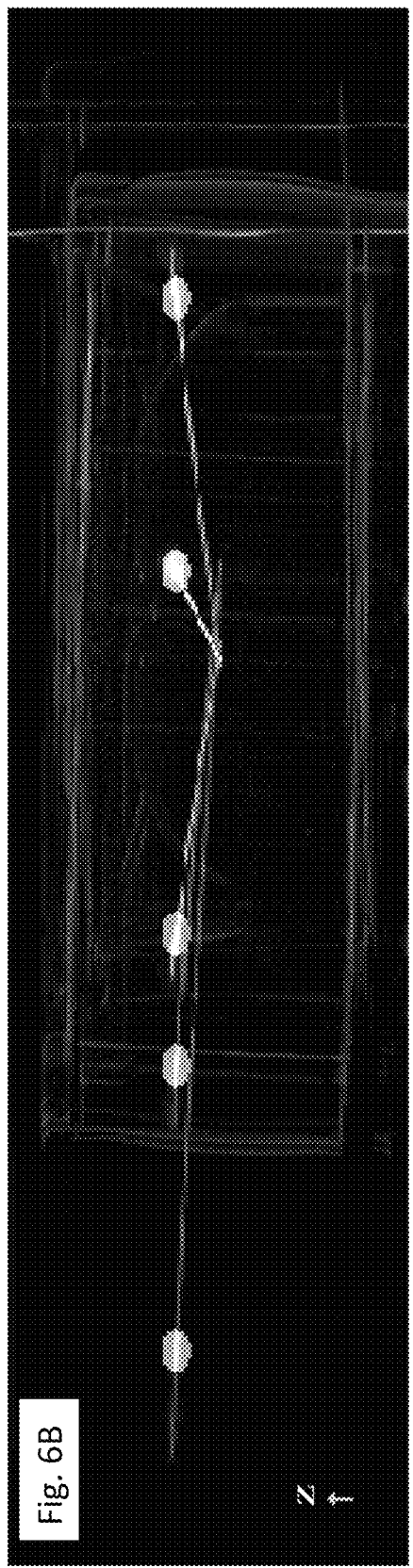
Fig. 6A
Fig. 6B

Table 2 Summary of experimental results. L/S stands for long/short needle, respectively. The bottom part of the table shows means and standard deviations across the long, short, and all scans in the dataset

| Scan ID | Reg. error (mm) | Marker error (mm) | Tip error (mm) | Trajectory error (mm) |
|---|---|---|---|---|
| L1 | 1.4 | 1.9 | 2.6 | 0.7 |
| L2 | 0.7 | 0.8 | 1.9 | 0.6 |
| L3 | 0.6 | 0.3 | 4.3 | 0.9 |
| L4 | 1.0 | 0.8 | 2.0 | 0.5 |
| S1 | 1.4 | 1.1 | 2.4 | 0.5 |
| S2 | 1.2 | 1.5 | 1.4 | 0.6 |
| S3 | 1.5 | 0.9 | 2.2 | 0.9 |
| L | 0.9 ± 0.4 | 1.0 ± 0.7 | 2.7 ± 1.1 | 0.7 ± 0.2 |
| S | 1.4 ± 0.2 | 1.2 ± 0.3 | 2.0 ± 0.5 | 0.7 ± 0.2 |
| ALL | 1.1 ± 0.4 | 1.0 ± 0.5 | 2.4 ± 0.9 | 0.7 ± 0.2 |

Fig. 11

METHOD OF NEEDLE LOCALIZATION VIA PARTIAL COMPUTERIZED TOMOGRAPHIC SCANNING AND SYSTEM THEREOF

TECHNICAL FIELD

The presently disclosed subject matter relates to computerized tomographic imaging and, more particularly, to interventional CT procedures.

BACKGROUND

Computed Tomography (CT) is nowadays widely available and pervasive in routine clinical practice. Computed tomography (CT) imaging produces a 3D map of the scanned object, where the different materials are distinguished by their X-ray attenuation properties. In medicine, such a map has a great diagnostic value, making the CT scan one of the most frequent non-invasive exploration procedures practiced in almost every hospital. The number of CT scans acquired worldwide is now in the tens of millions per year and is growing at a fast pace.

A CT image is produced by exposing the patient to many X-rays with energy that is sufficient to penetrate the anatomic structures of the body. The attenuation of biological tissues is measured by comparing the intensity of the X-rays entering and leaving the body. It is now believed that ionizing radiation above a certain threshold may be harmful to the patient. The reduction of radiation dose of CT scans is nowadays an important clinical and technical issue. In CT imaging, a basic trade-off is between radiation dose and image quality.

Interventional CT procedures are nowadays common and rapidly increasing. During the intervention, CT imaging is repeatedly performed to determine the location of an incrementally inserted instrument (such as a needle) relative to the patient anatomy. Various methods for needle guidance responsive to the CT imaging are described in the following paragraphs.

Since the needle is localized in image space, the needle is often required to be inserted in the axial imaging (in-plane insertion), which forces the radiologist to adjust the gantry angle repeatedly and rescan until a suitable orientation is found (cf. C. Walsh, B. Sapkota, M. Kalra, N. Hanumara, B. Liu, J. Shepard, R. Gupta, "Smaller and deeper lesions increase the number of acquired scan series in CT-guided lung biopsy". J Thorac Imaging. 26(3):196-203, 2011).

Steering the needle inside the tissue toward the target can be achieved manually by the radiologist under passive guidance, or by robotic steering in closed loop with the imaging. A commercial CT navigation device, SimpliCT by NeoRad (http://neorad.no/products_1/simplict_for_ct_and_pet_ct/) offers laser steering to guide the radiologist during manual insertion by aligning the needle with the laser direction.

In a paper (T. Schubert, A. L. Jacob, M. Pansini, D. Liu, A. Gutzeit, S. Kos, "CT-guided interventions using a freehand, optical tracking system: initial clinical experience", Cardiovascular and interventional radiology, 36(4), 1055-106, 2013) the authors describe an optical tracking system which uses surface markers to allow feedback of the needle orientation during the intervention.

Another approach is to optically overlay the CT image on top of the patient using a semitransparent mirror, thereby providing the physician with visual guidance during manual needle insertion (G. Fichtinger, A. Deguet, K. Masamune, E. Balogh, G. S. Fischer, H. Mathieu, L. M. Fayad. "Image overlay guidance for needle insertion in CT scanner". IEEE Transactions on Biomedical Engineering, 52(8), 1415-1424, 2005).

There also exists a robotic steering method (D. Glozman, M. Shoham. "Image-guided robotic flexible needle steering". IEEE Transactions on Robotics 23(3): 459-467, 2007), which drives the needle based on a tissue interaction model and in-plane imaging to provide feedback for closed loop control of the insertion.

Problems of computerized tomography-based inserted instrument location determination have been recognized in the conventional art and various techniques have been developed to provide solutions. For example:

Methods and systems for image-guided surgical interventions. Susil et. al. U.S. Pat. No. 7,225,012.

Susil teaches a method that utilizes a fiducial frame consisting of three N-shaped elements attached to an instrument, and operates in image space. A single CT slice is imaged and the image plane points of intersection with the fiducial frame allow computation of the instrument position in physical space.

Image guided surgery with dynamic image reconstruction, Eric C. Leuthardt et. al. U.S. Pat. No. 9,076,203.

Leuthardt teaches a method that dynamically generates images of two or more fiducials in an image. The method performs image registration based on fiducials in image space.

Methods, apparatuses, and systems useful in conducting image guided interventions. Jerome Edwards. US Patent Application No. 2005/0038337.

Edwards teaches a method which tracks a spherical marker inside the body on an organ/region that may move. The method requires a full image acquisition to locate the marker, so it is not useful for dose reduction on CT images. The method operates in image space.

The references cited above teach background information that may be applicable to the presently disclosed subject matter. Therefore the full contents of these publications are incorporated by reference herein where appropriate for appropriate teachings of additional or alternative details, features and/or technical background.

GENERAL DESCRIPTION

In CT imaging, a basic trade-off is between radiation dose and image quality. Lower doses produce imaging artifacts and increased noise, thereby reducing the image quality and limiting clinical usefulness. This issue is exacerbated in interventional CT, where repeated scanning is performed during an intervention. Since CT imaging exposes the patient to substantial X-rays ionizing radiation, radiation dose reduction is beneficial.

The present subject matter describes a new method for instrument (e.g. needle) and patient tracking in interventional CT procedures based on fractional CT scanning. The method can increase the accuracy with which a needle is located relative to the patient in the CT scanner coordinate frame—without performing reconstruction of the CT image. By performing fractional CT scanning the radiation dose associated with each needle localization can be reduced.

In some embodiments of the present subject matter, the method is to detect the needle and spherical marker in projection (sinogram) space—based on the needle's strong X-ray signal, its thin cylinder geometry, and a spherical marker mounted on the needle. Subsequently, a transformation from projection space to physical space can uniquely determine the location and orientation of the needle and the needle tip position within the patient.

According to one aspect of the presently disclosed subject matter there is provided a method of locating a tip of a metallic instrument inserted in a body, wherein the method utilizes a baseline sinogram derived from a prior computerized tomography (CT) scanning of the body, and wherein the baseline sinogram comprises projections in N exposure directions, the method comprising:

a) performing, by a computer, three-dimensional Radon space registration of a sparse repeat sinogram to the baseline sinogram, thereby giving rise to registration parameters, wherein the sparse repeat sinogram is derived from a repeat CT scanning of the body and comprises projections in n exposure directions, n being substantially less than N, and wherein the repeat CT scanning is provided with the metallic instrument inserted into the body, the metallic instrument having an attached marker located at a known distance from the instrument tip;

b) subtracting, by the computer, the baseline sinogram from the repeat sinogram in accordance with the registration parameters to obtain projection difference images, wherein each of the projection difference images is associated with an exposure direction of a respective projection in the repeat sinogram; and c) using, by the computer, the projection difference images and the known distance of the attached marker from the metallic instrument tip to determine a three-dimensional location of the metallic instrument tip.

In addition to the above features, the method according to this aspect of the presently disclosed subject matter can comprise one or more of features (i) to (xi) listed below, in any desired combination or permutation which is technically possible:

(i) further comprising: displaying data indicative of the determined three-dimensional location of the instrument tip.

(ii) wherein the determining a three-dimensional location of the metallic instrument tip comprises:
  i. using projection difference images to identify a three-dimensional location of the marker;
  ii. using the identified three-dimensional location of the marker and the projection difference images to identify a trajectory of the metallic instrument; and
  iii. determining the location of the instrument tip in accordance with, at least, the identified three-dimensional location of the marker, identified instrument trajectory and the known distance of the marker from the tip.

(iii) wherein the displaying data indicative of the determined three-dimensional location of the instrument tip comprises displaying a volume reconstruction in accordance with the baseline sinogram.

(iv) wherein the marker is spherical, and wherein the identifying a three-dimensional location of the spherical marker comprises:
  i) identifying, in each of at least two projection difference images, a projection of the spherical marker;
  ii) computing a two-dimensional center coordinate location of at least two identified projections of the marker; and
  iii) calculating a three-dimensional location of the spherical marker according to, at least, at least two computed two-dimensional center coordinate locations.

(v) wherein the identifying a trajectory of the metallic instrument comprises:
  i) identifying, for at least two projection difference images, a direction maximizing an accumulated intensity along the direction, thereby giving rise to at least two identified projections of the metallic instrument;
  ii) determining at least two instrument projection planes according to, at least:
    a. a line derived from a respective identified projection of the metallic instrument, and
    b. a geometry of a CT scanner, and
  iii) calculating a trajectory of the metallic instrument according to, at least, at least two determined instrument projection planes.

(vi) wherein the identifying a projection of the spherical marker in a projection difference image comprises performing two-dimensional cross-correlation of the projection difference image with a circular pattern.

(vii) wherein the identifying a projection of the spherical marker in a projection difference image comprises processing of the projection difference image by a neural network.

(viii) wherein the calculating a three-dimensional location of the spherical marker comprises:
  solving a system of projection matrix equations,
  wherein each projection matrix equation comprises a matrix determined according to, at least:
    i. a geometry of a CT scanner;
    ii. the computed center coordinate location of a projection difference image; and
    iii. the exposure direction of the projection difference image.

(ix) wherein the calculating the trajectory of the metallic instrument comprises:
  solving a system of equations,
  wherein each equation comprises a scalar product of an orientation vector with a normal vector of an instrument projection plane,
  thereby giving rise to data informative of the trajectory of the metallic instrument.

(x) wherein the metallic instrument is flexible, and wherein the calculating the trajectory of the metallic instrument comprises:
  i. determining an initial series of instrument segment points;
  ii. calculating a three-dimensional curve according to the series of instrument segment points;
  iii. determining a next direction according to, at least, a projection of the calculated three-dimensional curve onto at least one projection difference image;
  iv. identifying a next segment point according to, at least, the determined next direction and a segment length, thereby extending the series of segment points;
  v. recalculating the three-dimensional curve according to the extended series of segment points; and
  vi. repeating iii)-v) until a sum of distances between segment points of the series of segment points meets the known distance of the attached marker from the instrument tip.

(xi) wherein the three-dimensional curve is a Bezier curve.

According to another aspect of the presently disclosed subject matter there is provided a computer-based volume reconstruction unit configured to operate in conjunction with a CT scanner, the volume reconstruction unit comprising a processing and memory circuitry, the processing and memory circuitry being configured to perform a method of locating a tip of a metallic instrument inserted in a body, wherein the method utilizes a baseline sinogram derived from a prior computerized tomography (CT) scanning of the body, and wherein the baseline sinogram comprises projections in N exposure directions, the method comprising:
  a) performing, by a computer, three-dimensional Radon space registration of a sparse repeat sinogram to the baseline sinogram, thereby giving rise to registration parameters,
    wherein the sparse repeat sinogram is derived from a repeat CT scanning of the body and comprises projections in n exposure directions, n being substantially less than N, and wherein the repeat CT scanning is provided with the metallic instrument inserted into the body, the metallic instrument having an attached marker located at a known distance from the instrument tip;
  b) subtracting, by the computer, the baseline sinogram from the repeat sinogram in accordance with the registration parameters to obtain projection difference images, wherein each of the projection difference images is associated with an exposure direction of a respective projection in the repeat sinogram; and
  c) using, by the computer, the projection difference images and the known distance of the attached marker from the metallic instrument tip to determine a three-dimensional location of the metallic instrument tip.

In addition to the above features, the volume reconstruction unit according to this aspect of the presently disclosed subject matter can comprise one or more of features (i) to (vi) listed below, in any desired combination or permutation which is technically possible:
  (i) wherein the method of locating a tip of a metallic instrument further comprises:
    displaying data indicative of the determined three-dimensional location of the instrument tip.
  (ii) wherein the determining a three-dimensional location of the metallic instrument tip comprises:
    i. using projection difference images to identify a three-dimensional location of the marker,
    ii. using the identified three-dimensional location of the marker and the projection difference images to identify a trajectory of the metallic instrument; and
    iii. determining the location of the instrument tip in accordance with, at least, the identified three-dimensional location of the marker, identified instrument trajectory and the known distance of the marker from the tip.
  (iii) wherein the marker is spherical, and wherein the identifying a three-dimensional location of the spherical marker comprises:
    i) identifying, in each of at least two projection difference images, a projection of the spherical marker;
    ii) computing a two-dimensional center coordinate location of at least two identified projections of the marker; and
    iii) calculating a three-dimensional location of the spherical marker according to, at least, at least two computed two-dimensional center coordinate locations.
  (iv) wherein the identifying a trajectory of the metallic instrument comprises:
    i) identifying, for at least two projection difference images, a direction maximizing an accumulated intensity along the direction, thereby giving rise to at least two identified projections of the metallic instrument;
    ii) determining at least two instrument projection planes according to, at least:
      a. a line derived from a respective identified projection of the metallic instrument, and
      b. a geometry of a CT scanner, and
    iii) calculating a trajectory of the metallic instrument according to, at least, at least two determined instrument projection planes.
  (v) wherein the calculating the trajectory of the metallic instrument comprises:
    solving a system of equations,
    wherein each equation comprises a scalar product of an orientation vector with a normal vector of an instrument projection plane,
    thereby giving rise to data informative of the trajectory of the metallic instrument.
  (vi) wherein the metallic instrument is flexible, and wherein the calculating the trajectory of the metallic instrument comprises:
    i. determining an initial series of instrument segment points;
    ii. calculating a three-dimensional curve according to the series of instrument segment points;
    iii. determining a next direction according to, at least, a projection of the calculated three-dimensional curve onto at least one projection difference image;
    iv. identifying a next segment point according to, at least, the determined next direction and a segment length, thereby extending the series of segment points;
    v. recalculating the three-dimensional curve according to the extended series of segment points; and
    vi. repeating iii)-v) until a sum of distances between segment points of the series of segment points meets the known distance of the attached marker from the instrument tip.

According to another aspect of the presently disclosed subject matter there is provided a computer program product implemented on a non-transitory computer usable medium having computer readable program code embodied therein to cause the computer to perform a method of locating a tip of a metallic instrument inserted in a body, wherein the method utilizes a baseline sinogram derived from a prior computerized tomography (CT) scanning of the body, and wherein the baseline sinogram comprises projections in N exposure directions, the method comprising:
  a) performing, by a computer, three-dimensional Radon space registration of a sparse repeat sinogram to the baseline sinogram, thereby giving rise to registration parameters,
    wherein the sparse repeat sinogram is derived from a repeat CT scanning of the body and comprises projections in n exposure directions, n being substantially less than N, and wherein the repeat CT scanning is provided with the metallic instrument inserted into the body, the metallic instrument having an attached marker located at a known distance from the instrument tip;
  b) subtracting, by the computer, the baseline sinogram from the repeat sinogram in accordance with the registration parameters to obtain projection difference images, wherein each of the projection difference images is associated with an exposure direction of a respective projection in the repeat sinogram; and c) using, by the computer, the projection difference images and the known distance of the attached marker from the metallic instrument tip to determine a three-dimensional location of the metallic instrument tip.

Advantages of this method include: reducing the patient's radiation exposure via the use of fractional scanning while maintaining high image quality, faster operation due to performing calculations in sinogram space, and enabling the patient registration and needle localization methods to be performed simultaneously.

BRIEF DESCRIPTION OF THE DRAWINGS

In order to understand the invention and to see how it can be carried out in practice, embodiments will be described, by way of non-limiting examples, with reference to the accompanying drawings, in which:

FIG. 6a is an illustration of the marker location as intersection of rays (left) and needle orientation as intersection of planes (right).

FIG. 6b illustrates an overlay of several representative fractional projection difference images showing both the needle and the marker as a circle and line (bright pixels) intersecting it;

FIG. 11 summarizes the results of the flexible needle tip localization for seven CT scans.

DETAILED DESCRIPTION

Figure 1A:
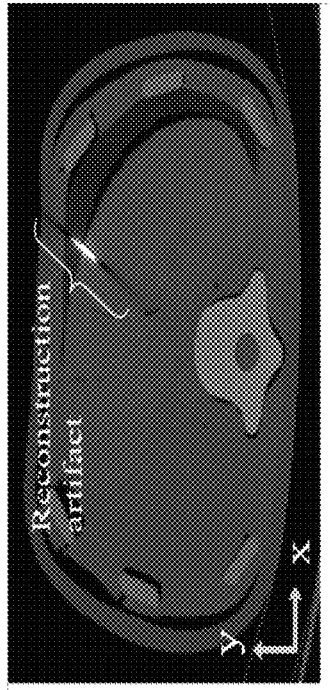
FIG. 1a illustrates a needle inserted into an abdominal phantom on CT scanner bed.
Figure 1B:
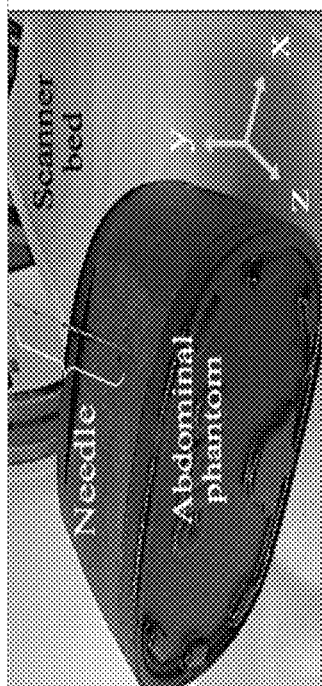
FIG. 1b illustrates a reconstruction artifact caused by presence of the metallic needle, in an axial view.

In the following detailed description, numerous specific details are set forth in order to provide a thorough understanding of the invention. However, it will be understood by those skilled in the art that the presently disclosed subject matter may be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "processing", "computing", "representing", "comparing", "generating", "matching", or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities including, by way of non-limiting example, the Volume Reconstruction Unit disclosed in the present application.

The terms "non-transitory memory" and "non-transitory storage medium" used herein should be expansively construed to cover any volatile or non-volatile computer memory suitable to the presently disclosed subject matter.

The operations in accordance with the teachings herein may be performed by a computer specially constructed for the desired purposes or by a general-purpose computer specially configured for the desired purpose by a computer program stored in a non-transitory computer-readable storage medium.

Embodiments of the presently disclosed subject matter are not described with reference to any particular programming language. It will be appreciated that a variety of programming languages may be used to implement the teachings of the presently disclosed subject matter as described herein.

For purpose of illustration only, the following description is provided for a parallel-beam scanning. Those skilled in the art will readily appreciate that the teachings of the presently disclosed subject matter are, likewise, applicable to fan-beam and cone-beam CT scanning.

When imaging a metallic object, detector elements of a CT scanner which are behind the object relative to the X-ray source suffer from beam hardening or photon starvation, i.e., low energy photons are more easily attenuated by the metal, resulting in the detected number of photons not following the simple exponential decay of soft tissue attenuation (cf. F. E. Boas, D. Fleischmann. "CT artifacts: causes and reduction techniques." *Imaging Med.* 4(2):229-240, 2012). Consequently a signal in projection space might not represent the true attenuation integral of the source-detector ray path. As a result, image reconstruction based on this starved signal may produce non-local streak imaging artifacts which obscure the details of the metal object and its surroundings.

Figure 1C:
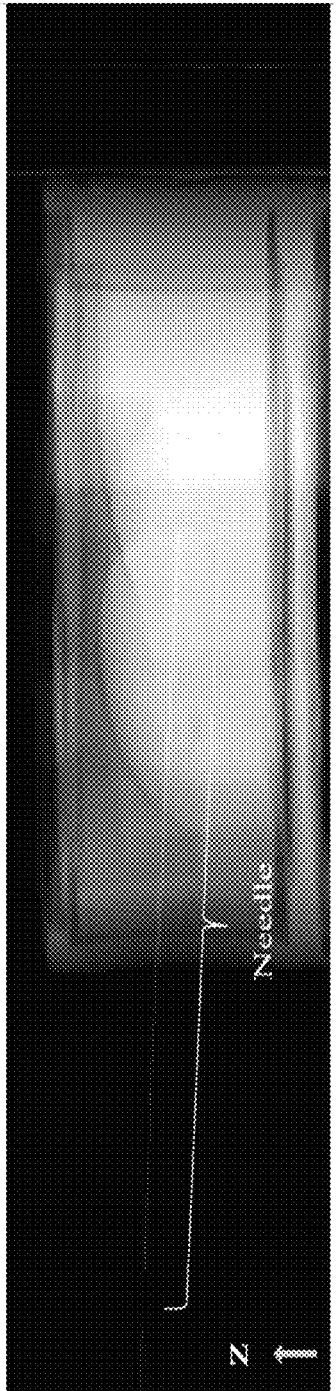
FIG. 1c illustrates a single projection view showing the needle inserted into the phantom.
Figure 1D:
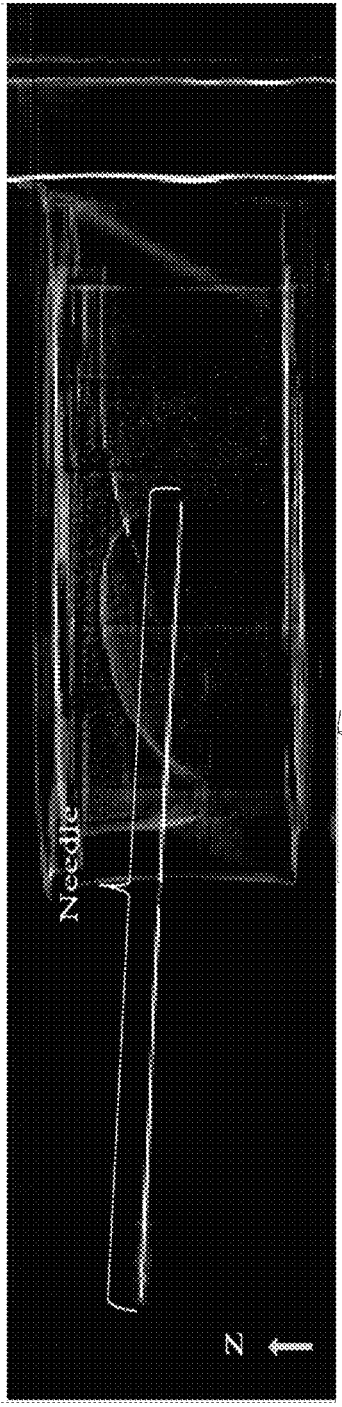
FIG. 1d illustrates a projection difference between repeat scan with needle and an aligned baseline scan for same view.

In contrast, in projection space, photon starvation artifacts caused by metallic elements are local in nature. Thus, they can be accurately detected as the difference between a baseline projection in which the needle is absent, and an aligned repeat scan projection in which the needle is present (see FIG. 1c). Furthermore, the repeat scan can be of a lower dose, limited scanning range and/or subsampled from selective views, since reconstruction of the repeat scan is not required. In some embodiments of the present subject matter, it is possible to take advantage of the strong needle signal in projection space in order to locate the needle and then transform its location in physical space based on the scanner imaging characteristics.

Figure 2A:
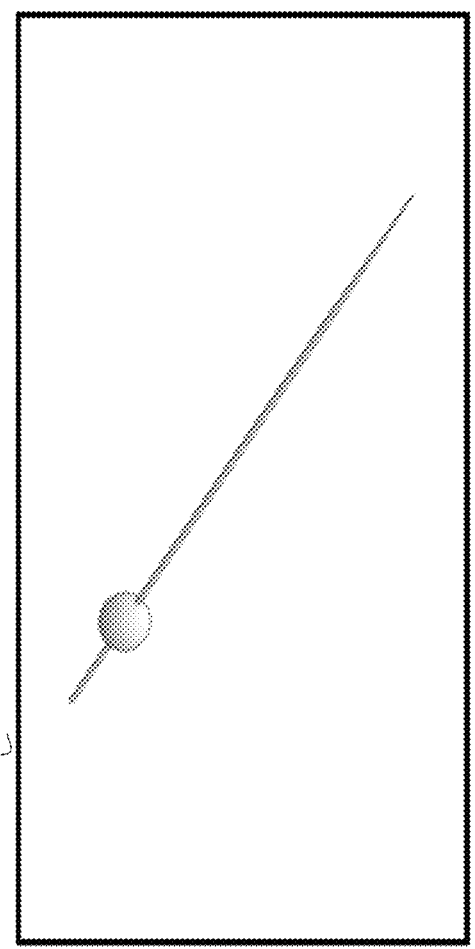
FIG. 2a illustrates a model of a needle with a spherical marker of the type utilized in some embodiments of the present subject matter.
Figure 2B:
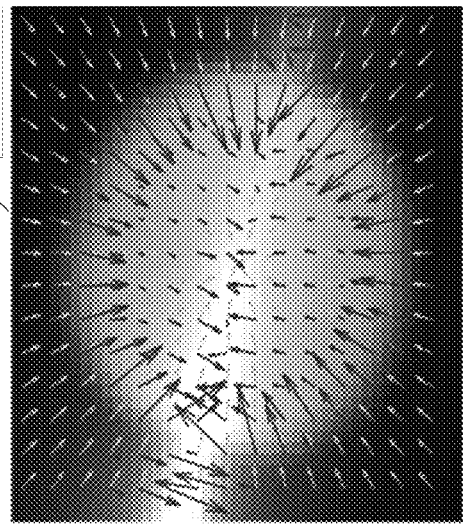
FIG. 2b illustrates a reconstruction artifact caused by the presence of the metallic needle, in an axial view.
Figure 2C:
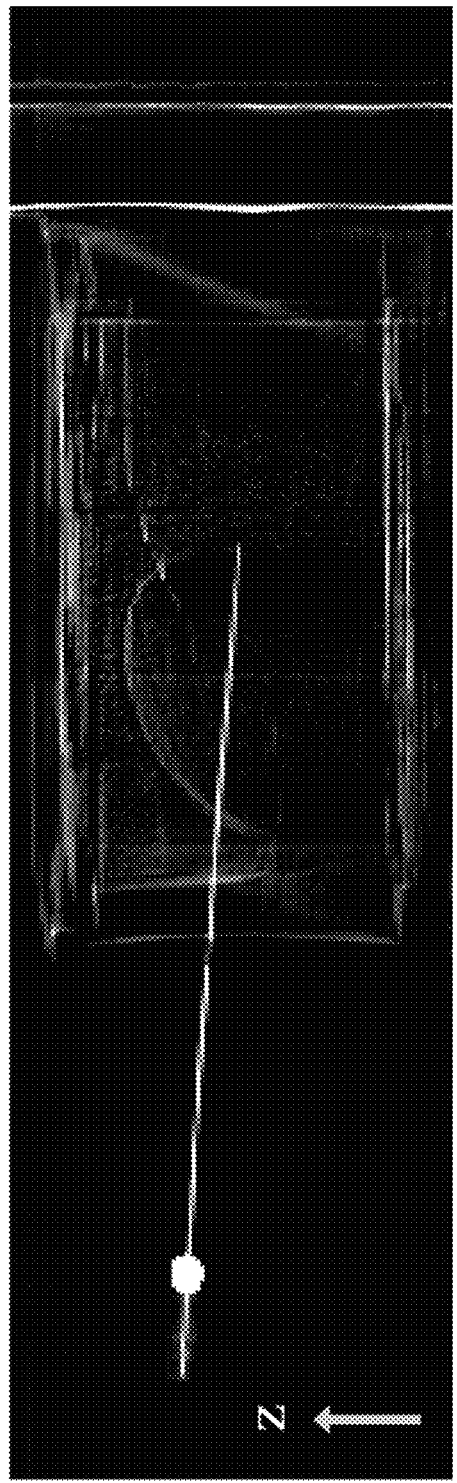
FIG. 2c illustrates a projection difference image for single view.

Detectors which record a highly attenuated signal due to a metal element blocking the ray from the source can be identified and localized by comparing the fractional repeat scan projection data to the baseline projection using 3D rigid registration parameters. Then it is possible to compute a re-projection of the baseline CT scan such that the re-projected baseline data is aligned with the fractional repeat scan projection data of the inserted needle. For each view angle, we can then obtain a 2D projection difference image by subtracting the aligned projections so that only the differences are visible, most prominently the needle with spherical marker. The size (in pixels) of this image is determined by the size of detector array, in which detectors readings are higher where their corresponding source-to-detector ray passes through the needle (See FIG. 2c).

Figure 3:
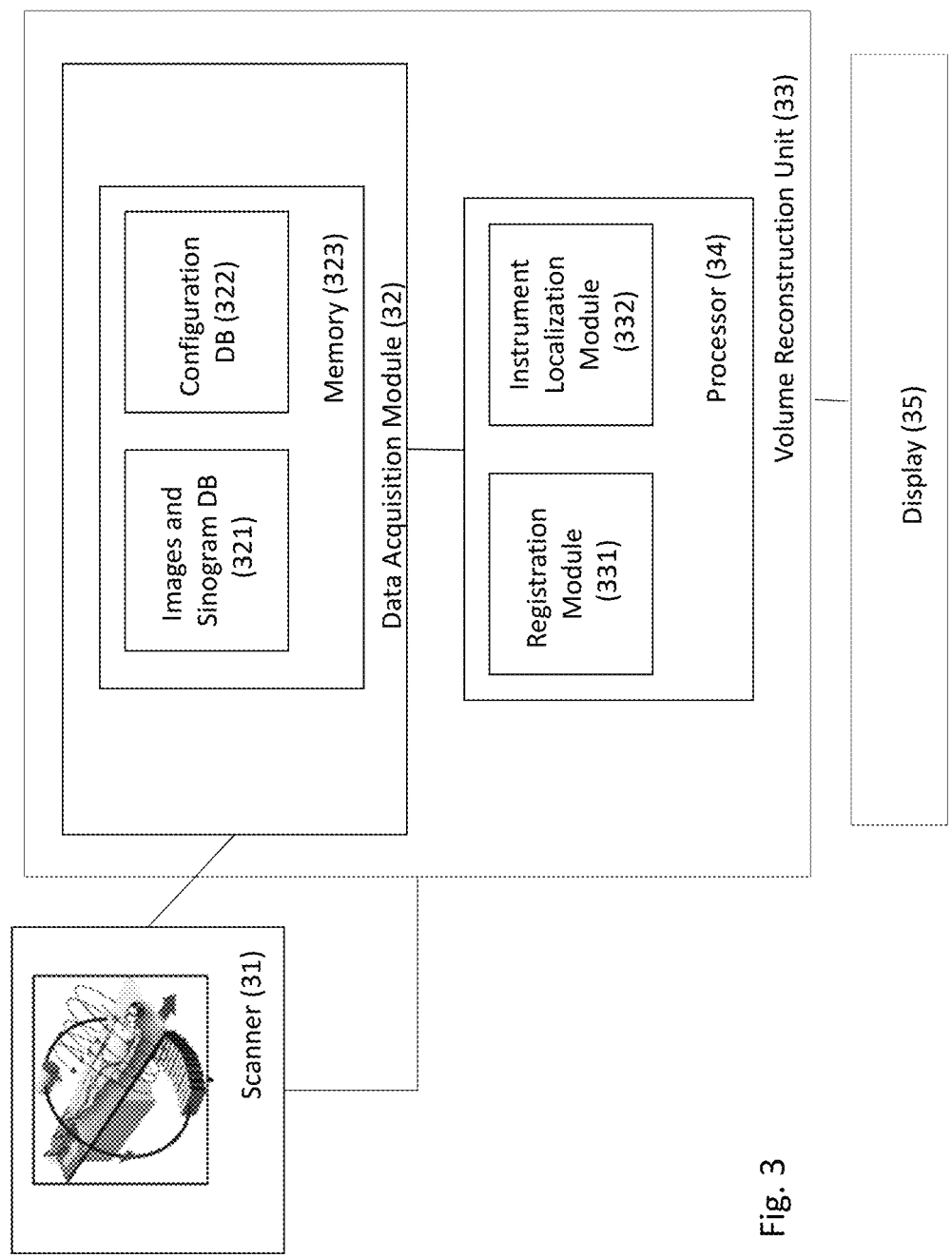
FIG. 3 illustrates a functional block diagram of an example CT scanning system in accordance with certain embodiments of the presently disclosed subject matter.

Attention is now drawn to FIG. 3 illustrating an example functional diagram of a CT repeat scanning system with needle localization capabilities—in accordance with some embodiments of the presently disclosed subject matter.

The CT scanning system can include a CT scanner (31) which can be configured to provide selective repeat scanning. CT scanner (31) can be operably coupled to a volume reconstruction unit (33).

Volume reconstruction unit (33) can include a data acquisition module (32) which can be configured to acquire data indicative of 3D projective measurements made by the scanner (31), and to generate corresponding sinograms. In some embodiments, the data acquisition module can receive sinograms directly from the CT scanner (31). The generated sinograms (e.g. a baseline sinogram, partial sinograms from repeat scans, etc.) can be stored—for example—in a memory (323) comprising an image and sinogram database (321). The database (321) can further accommodate baseline and repeat images if obtained by the data acquisition module. The memory (323) can be further configured to accommodate a configuration database (322) storing data informative of scan parameters and reconstruction models usable during the volume reconstruction.

The volume reconstruction unit (33) can further include a processing and memory circuitry (34) operably coupled to the data acquisition module (32). Processing and memory circuitry (34) can be configured to receive sinograms from the data acquisition module (32), and to perform processing in accordance with methods described hereinbelow.

Processing and memory circuitry (34) can include, for example, a processor (342) operably coupled to a memory (344). Processor (342) can be a hardware-based electronic device with data processing capabilities, such as, for example, a general purpose processor, a specialized Application Specific Integrated Circuit (ASIC), one or more cores in a multicore processor etc. A processor (342) can also consist, for example, of multiple processors, multiple ASICs, virtual processors, combinations thereof etc.

A memory (344) can be, for example, any kind of volatile or non-volatile storage, and can include, for example, a single physical memory component or a plurality of physical memory components. The memory (344) can be configured to store various data used in computation.

As will be further detailed hereinbelow with reference to FIG. 5 and FIGS. 9-10, the processing circuitry (34) can be configured to execute several functional modules in accordance with computer-readable instructions implemented on a non-transitory computer-readable storage medium. Such functional modules are referred to hereinafter as comprised in the processing and memory circuitry. These modules can include, for example, Registration Unit (331), and Instrument Localization Unit (332).

Registration Unit (331) can be configured to provide registration of the baseline scan to the patient by aligning the full baseline sinogram to the partial sinogram obtained by fractional scanning.

Registration Unit (331) can be configured to perform a Radon-space rigid registration method (such as the method described in: G. Medan, N. Shamul, L. Joskowicz. "Sparse 3D Radon space rigid registration of CT scans: method and validation study". *IEEE Transactions on Medical Imaging*, accepted October 2016) which computes the rigid registration transformation between a baseline scan and a sparse repeat scan. The Radon-space rigid registration method works by matching one-dimensional projections obtained via summation along parallel planes of both the baseline scan and the repeat scan, in a 3D extension of the 2D Radon transform. The calculation is performed entirely in projection space, and the matching is done based on maximization of normalized cross correlation. The matched projections are then used in order to construct a set of equations, the solution of which gives the parameters of the rigid registration between the scans.

As will be further detailed below with reference to FIG. 5, Instrument Localization Unit (332) can be configured to create projection difference images from a baseline sinogram and a partial sinogram obtained by fractional scanning.

Instrument Localization Unit (332) can be further configured to detect—in projection difference images—detector patterns corresponding to a metallic instrument (e.g. needle) with an attached spherical marker that has been inserted into a previously scanned body prior to repeat sparse scanning.

Instrument Localization Unit (332) can be further configured to compute the 3D location of a metallic instrument inserted within the scanned physical body, and to calculate the 3D location of the instrument's tip.

The processing circuitry (34) can be further configured to process the computed instrument location data together with an image of the body resulting from the baseline scan, and to compose an image of the body which includes the inserted instrument. The processing circuitry (34) can transfer the resulting image for rendering at a display (35) coupled to the volume reconstruction unit (33).

It is noted that the teachings of the presently disclosed subject matter are not bound by the specific CT scanning system described with reference to FIG. 3. Equivalent and/or modified functionality can be consolidated or divided in another manner and can be implemented in any appropriate combination of software, firmware and hardware.

Figure 4:
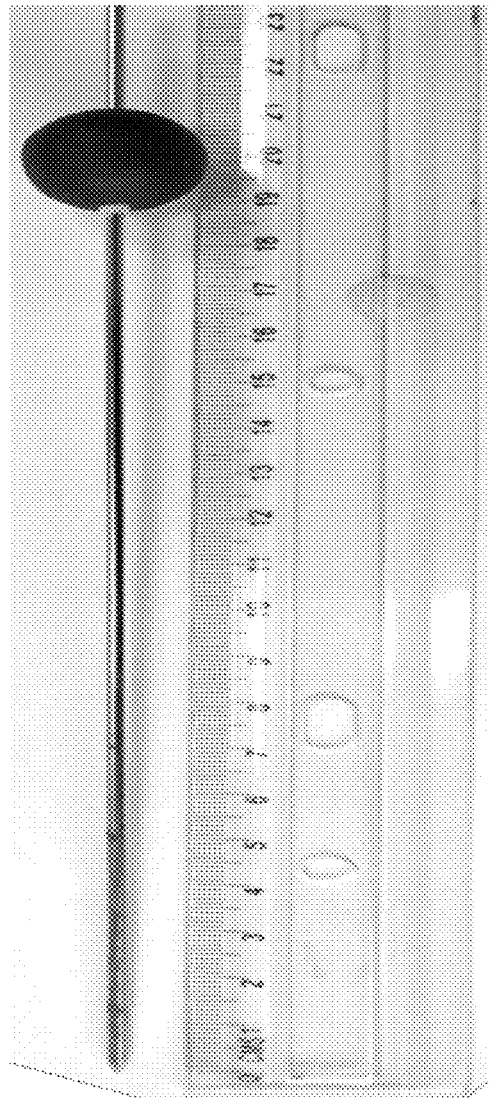
FIG. 4 illustrates a non-limiting example of a needle with a spherical marker attached to it at a known distance from the needle tip in accordance with certain embodiments of the presently disclosed subject matter.

Next, attention is drawn to FIG. 4, which depicts an example metallic needle with a spherical marker attached to it at a known distance from the needle tip—in accordance with certain embodiments of the presently disclosed subject matter.

In a projection difference image, data in the vicinity of the needle tip can be noise-prone and can suffer from partial volume effect since the slice intervals and/or the slice thickness is a few millimeters, which is often greater than the required accuracy.

Accordingly, a sphere with a diameter larger than the needle diameter can be attached to the needle. The sphere can be rigidly attached at a known distance from the needle tip, with this known distance being larger than the expected insertion depth of the needle into the patient's body. In some embodiments, the sphere is composed of ceramic material. In some embodiments, the diameter of the sphere is several times larger than the needle diameter. In some embodiments, the needle is composed of titanium. The spherical marker can be attached, for example, at one end of the needle, or at a point along the length of the needle.

The sphere, which remains outside the patient body, can appear as a circle in projection space, and can be identifiable in a projection difference image, for example by using pattern matching techniques, as described in detail below with reference to FIG. 5. The identified sphere and the needle can then be accurately localized in physical space, and the tip position in physical space can then be determined—as described in detail below with reference to FIG. 5.

Figure 5:
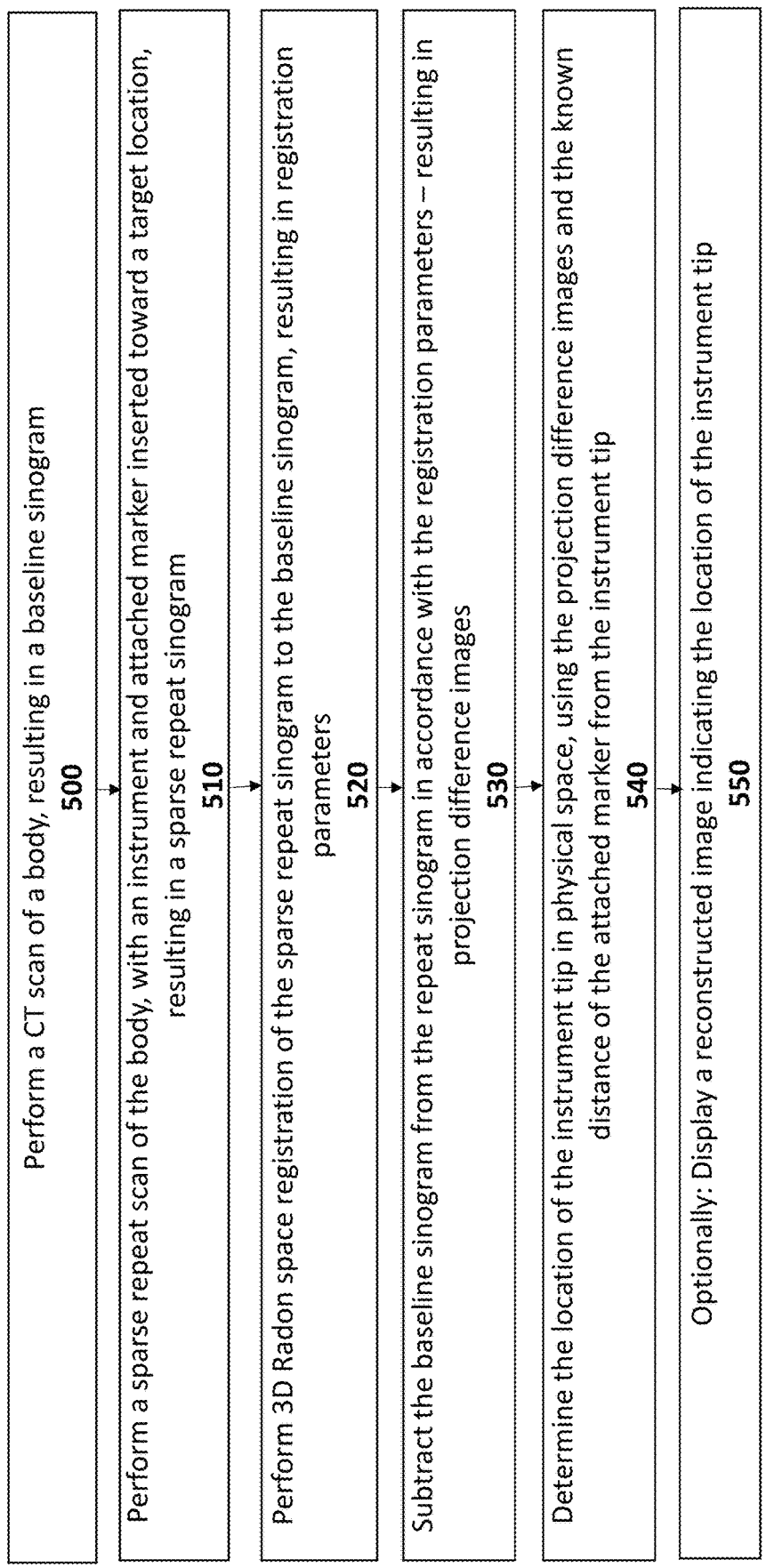
FIG. 5 illustrates a generalized flow-chart of needle localization using fractional scanning in accordance with certain embodiments of the presently disclosed subject matter.

Attention is now directed to FIG. 5, which depicts a flow chart of an example needle localization method in accordance with certain embodiments of the presently disclosed subject matter. The method can utilize a baseline sinogram obtained by a prior CT scanning of a body. This baseline sinogram can includes a particular number of exposure directions which is herein denoted as N.

Initially, a baseline CT scan can be performed (500) on a body. The body can be, for example, a patient in which the metallic instrument will be, for example, subsequently inserted in a progressive manner. This baseline CT scan can result in a baseline sinogram.

Next, a sparse repeat CT scan (also called a fractional scan) can be performed (510) on the body. In this scan the body can now have a metallic instrument (e.g. a surgical needle) inserted. The metallic instrument can have a marker (e.g. a spherical marker) attached. The tip of the metallic instrument can be located at a known distance from the marker. The needle with attached marker can be, for example, in conformance with the needle description provided above, with reference to FIG. 4. The sparse repeat scan can include substantially fewer exposure directions than the original CT scan. The sparse repeat scan can result in a sparse repeat sinogram. The letter m hereforward denotes the number of views in the sparse repeat scan. In this context, "substantially fewer" exposure directions means some number of directions less than N, but sufficient so as to enable determination of the instrument tip location with a level of accuracy meeting a usage-specific accuracy requirement.

The processing and memory circuitry (34) (for example: Registration Unit (331)) can then perform three-dimensional radon space registration (520) of the sinogram derived from the second scan to the sinogram of the first scan. The registration can be performed, for example, according to the method described in PCT application IL2015/050076, "METHOD OF REPEAT COMPUTER TOMOGRAPHY SCANNING AND SYSTEM THEREOF" by Joskowicz, Medan, Kronman. The registration can result in the determination of registration parameters.

The processing and memory circuitry (34) (for example: Instrument Localization Unit (331)) can next subtract (530) the baseline sinogram from the repeat sinogram in accordance with the determined registration parameters. The subtracting can then result in m two-dimensional images— each of which being associated with the exposure direction of the two-dimensional images from which it was derived. These images are herein termed projection difference images.

In some embodiments, processing and memory circuitry (34) (for example: Instrument Localization Unit (331)) creates projection difference images by computing a re-projection of the baseline CT scan such that the re-projected baseline data is aligned with the sparse repeat scan projection data including the inserted needle. For each exposure direction, the ILM can then obtain a 2D projection difference image by subtracting the aligned projections so that only the differences are visible—for example: the needle with spherical marker. The size (in pixels) of this image is determined by the size of detector array, in which detectors' readings are higher where their corresponding source-to-detector ray passes through the metallic needle (see FIG. 2b).

The processing and memory circuitry (34) (for example: Instrument Localization Unit (331)) can then determine (540) the location of instrument tip in physical space by using the projection difference images (for example: by determining the location of the attached marker and the trajectory of the needle in physical space) in conjunction with the known distance of the attached marker from the instrument tip.

Optionally, the processing and memory circuitry (34) (for example: Instrument Localization Unit (331)) can display (550) a reconstruction of the baseline scan indicating the determined location of the instrument tip. By way of non-limiting example, The processing and memory circuitry (34) (for example: Instrument Localization Unit (331)) can cause Display (15) to display a 2D multislice image or a 3D image of the body showing the needle in the calculated location and orientation. Alternatively, by way of non-limiting example, the processing and memory circuitry (34) (for example: Instrument Localization Unit (331)) can instead cause the display of numeric or textual data indicating the location of the instrument tip. In some embodiments, the processing and memory circuitry (34) (for example: Instrument Localization Unit (331)) can provide an indication of the location of the instrument tip to an operator without actually providing a reconstructed image.

It is noted that the teachings of the presently disclosed subject matter are not bound by the flow chart illustrated in FIG. 5, the illustrated operations can occur out of the illustrated order. For example, the subtraction (530) and localization (540) operations shown in succession can be executed substantially concurrently. It is also noted that whilst the flow chart is described with reference to elements of system depicted in FIG. 3, this is by no means binding, and the operations can be performed by elements other than those described herein.

Figure 9:
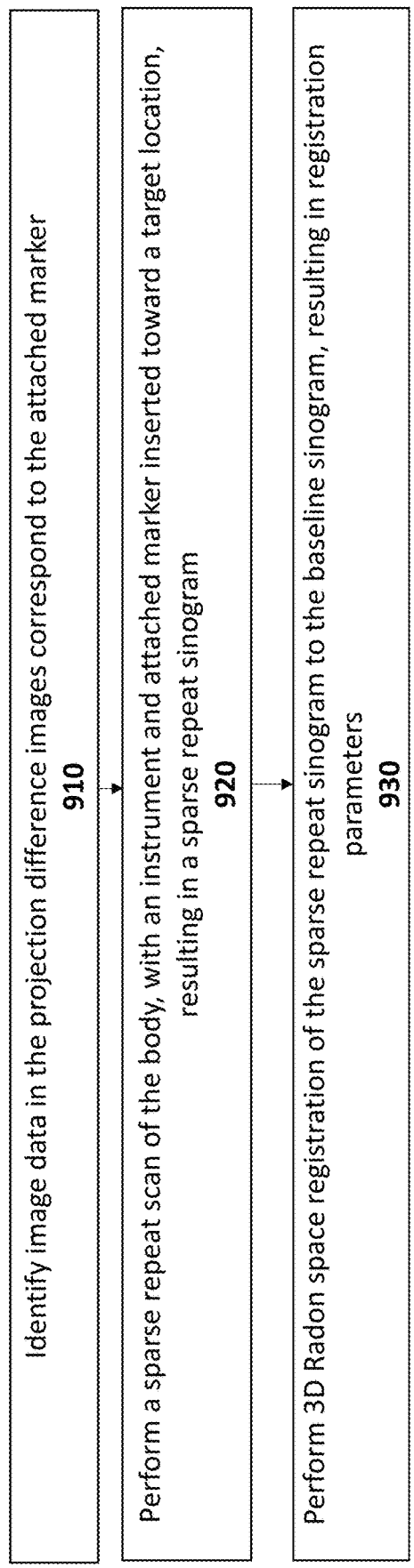
FIG. 9 illustrates a flow chart describing an example method for determining the location of the instrument tip in physical space using the projection difference images and the known distance of the instrument tip from the attached marker, according to some embodiments of the presently disclosed subject matter.

Attention is now drawn to FIG. 9, which illustrates a flow chart describing an example method for determining the location of the instrument tip in physical space using the projection difference images and the known distance of the instrument tip from the attached marker, according to some embodiments of the presently disclosed subject matter.

The processing and memory circuitry (34) (for example: Instrument Localization Unit (331)) can use projection difference images to identify (910) a three-dimensional location of the marker.

In some embodiments, the attached marker is spherical. By way of non-limiting example, the processing and memory circuitry (34) (for example: Instrument Localization Unit (331)) can perform the following sequence to identify the three-dimensional location of the marker:
  i) identifying, in each of at least two projection difference images, a projection of the spherical marker.
    In some embodiments, the processing and memory circuitry (34) (for example: Instrument Localization Unit (331)) can do this by matching each of two or more difference projection image with a circle pattern via two-dimensional cross-correlation.
    Alternatively, the processing and memory circuitry (34) (for example: Instrument Localization Unit (331)) can process each difference projection image with a machine learning module that has been trained to identify a projection of a spherical marker.
  ii) For at least two identified projections of the marker, computing a two-dimensional center coordinate location.
    The processing and memory circuitry (34) (for example: Instrument Localization Unit (331)) can do this—for example—by maximizing a cost function for each view (i.e. exposure direction) as follows:
    $c_i = \text{argmax}_{c \in \mathbb{R}^2} \Sigma_{x:||x-c|-R|<\epsilon} \nabla h_i(x) \cdot \hat{r}$
    where $h_i(x)$ is the projection difference image for view i, R is the known radius of the marker, and e is a small distance constant (0.5 mm), so that the gradient of the projection difference image is best aligned with the radial direction $\hat{r}=(x-c)/||x-c||$ inside a spherical shell of radius R and thickness $2\epsilon$. This cost function allows avoiding the high intensities due to the needle passing through the marker, while taking into account the relatively weaker gradients at the edge of the projected marker circle.
  iii) calculating a three-dimensional location of the spherical marker according to, at least, at least two computed two-dimensional center coordinate locations.
    In some embodiments, the 3D location can be determined solving a system of projection matrix equations, wherein each projection matrix equation comprises a matrix determined according to, at least:
      i. a geometry of a CT scanner;
      ii. the computed center coordinate location of a projection difference image; and
      iii. the exposure direction of the projection difference image.
    By way of non-limiting example, the processing and memory circuitry (34) (for example: Instrument Localization Unit (331)) can calculate this by, for example, solving an inverse problem using the known projection geometry of the CT and the localized marker centers described by transformation matrices Pj. The solution of the set of projection equations
    $\{P_j s = c_j\}\{P_j s = c_j\}_{j=1}^{K=1}$
    yields the 3D spherical marker center location s.

The processing and memory circuitry (34) (for example: Instrument Localization Unit (331)) can next use the identified three-dimensional location of the marker and the projection difference images to identify (920) a trajectory of the metallic instrument.

By way of non-limiting example, the processing and memory circuitry (34) (for example: Instrument Localization Unit (331)) can perform the following sequence to identify the trajectory of the metallic instrument:
  i) identifying for at least two projection difference images, a direction maximizing an accumulated intensity along the direction, thereby giving rise to at least two identified projections of the metallic instrument;
    By way of non-limiting example, the processing and memory circuitry (34) (for example: Instrument Localization Unit (331)) can fit a 2D line $l_i$ through the previously detected marker center $c_i$ in each projection difference image, so that line $l_i$ is aligned with the projection of the needle which appears as a high intensity thin line. To achieve this, the processing and memory circuitry (34) (for example: Instrument Localization Unit (331) can, for example, select the direction maximizing the accumulated intensity of the difference image along it.
    Specifically, the processing and memory circuitry (34) (for example: Instrument Localization Unit (331) can compute the line $l_i$ by maximizing the following cost function and finding its slope angle $\theta_i$:
    $\theta_i = \text{argmax } \Sigma_{x \in W_\theta} h_i(x)$
    where $W_\theta$ denotes a thin rotating window of width $\epsilon$ and length $D_{MT}$ (where $D_{MT}$ is the known marker center distance from the tip of the needle), which is rotated by an angle $\theta$ in 2D about its end $c_i$.
  ii) determining at least two instrument projection planes according to, at least:
    a. a line derived from a respective identified projection of the metallic instrument, and
    b. a geometry of a CT scanner.
    It is noted that each line $l_i$ in a 2D projection as described above defines a line $L_i$ on the plane of scanner detector elements in physical space through the elements associated with the line $l_i$. The set of rays between each detector element position on $L_i$ and the source position for view i define a needle projection plane $\Pi_i$ in physical space. In parallel beam geometry, the source position is located at infinity and the set of rays are parallel. In cone-beam geometry, the set of rays forms a fan emanating from the source. FIG. 6a illustrates the case of parallel beam geometry.
  iii) calculating a trajectory of the metallic instrument according to, at least, at least two determined instrument projection planes.
    In both parallel and cone beam geometries, the set of planes $\{\Pi_i\}$ forms a pencil of planes intersecting at a single line in physical space having an orientation vector $\hat{O}$, corresponding to the needle orientation. The plane normal vector is denoted as $\hat{n}_i$. Since $\hat{O}$ is contained in all planes $\{\Pi_i\}$, the following set of equations holds:
    $\hat{O}^T \hat{n}_i = 0, i = 1, \ldots, m$
    In some embodiments, the processing and memory circuitry (34) (for example: Instrument Localization Unit (331)) can compute the needle orientation in physical space by solving this over-constrained system of equations—for example by approximating the null-space of $N=[\hat{n}_1 \hat{n}_2 \ldots \hat{n}_m]^T$ using Singular Value Decomposition (SVD). Let $N = U\Sigma V^T$ where U, V are orthonormal matrices and $\Sigma$ has the singular values of N on its diagonal. Then, the columns of V corresponding to the smallest values on the diagonal of $\Sigma$ are the basis to the approximate null-space. Since the planes $\{\Pi_i\}$ intersect at a line, the null-space is one-dimensional line in 3D physical space. Therefore, the column of matrix V corresponding to the smallest singular value in E is the solution. To improve robustness, the ILM can use the Random Sample Consensus (RANSAC) scheme and compute the null-space for a random subset of rows of N at each iteration. The ILM can then select the result with most "supporters", i.e., the result for which most of the rows of N are nearly orthogonal to the considered null-space.

The processing and memory circuitry (34) (for example: Instrument Localization Unit (331)) can then determine (930) the location of the instrument tip in accordance with, at least, the identified three-dimensional location of the marker, identified instrument trajectory and the known distance of the marker from the tip.

In some embodiments, once the needle orientation and the marker position have been calculated, the processing and memory circuitry (34) (for example: Instrument Localization Unit (331)) can localize the tip by starting from the marker position and tracing the known distance between the tip and the marker along the needle orientation.

In some embodiments the needle is rigid. If so, then it can be modeled as a straight line, the tip position T is defined by:

$$T = M + D_{MT}\hat{O}$$

where $D_{MT}$ is the known marker center distance from the tip of the needle.

The method of FIG. 5 was tested on real CT scan data obtained using a GE Discovery CT750HD scanner to scan a CIRS Model 57 abdomen phantom with a 16 Gauge (1.65 mm diameter) 25 cm rigid needle with a spherical marker attached to it at 200 mm from the needle tip. The resulting dataset consists of 5 CT scans with both projection and image data of the abdomen phantom (FIG. 1a) scanned with a needle inserted at different locations, depths and at different global phantom positions, as well as one baseline scan without the needle present.

The reconstructed image size is 800×800×126 voxels, with spatial resolution of 0.58×0.58×1.25 mm³. The detector array consists of 885×126 elements scanned at 984 views at regular intervals in the range [0°, 360°], where for slices were acquired in each full revolution. The data was re-binned from fan-beam to parallel rays representation of the projections. The needle was rigid and 1.5 mm in diameter. The spherical marker has a diameter of 20 mm and was affixed at 200 mm from the tip.

Figure 7:
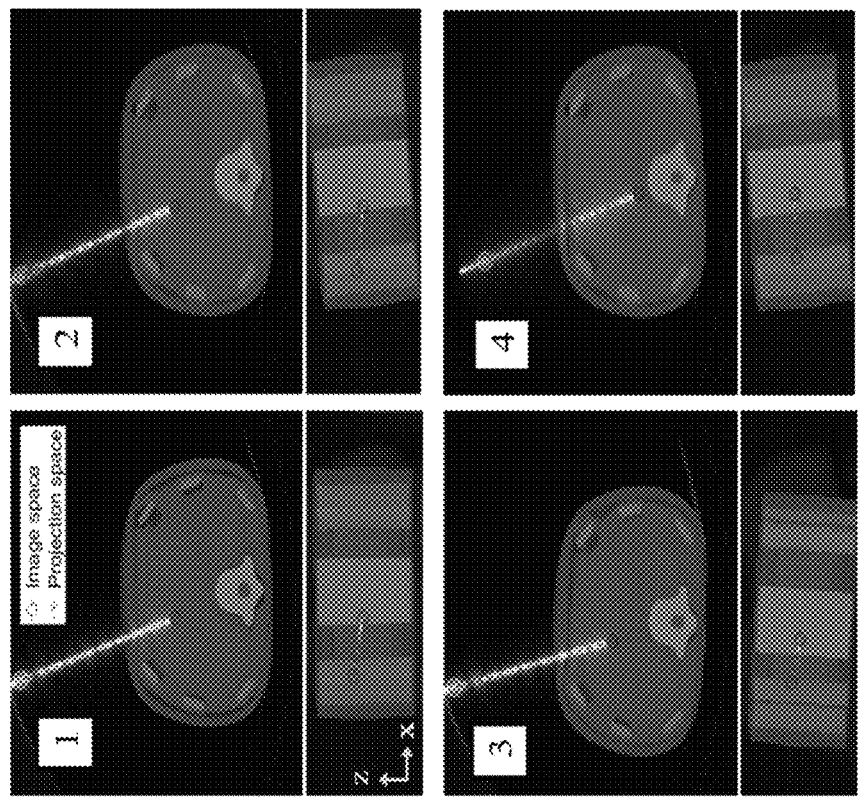
FIG. 7 illustrates projection-space estimated needle position, vs. image-space estimated needle position in the 5 scans of the dataset displayed as multi-slice images, in which a color map encodes the depth of each slice in the direction perpendicular to the image plane, the needle is shown as a bright line in a multi-slice image in axial and coronal views (top row and bottom row, respectively, and the needle localization is indicated as the circle and x marks at the ends of the colored lines, representing the marker center and tip position.

The projection datasets were processed as follows:
1. A full scan of the scanning bed without the phantom was subtracted from the other scans, in order to improve registration accuracy. Next, to simulate fractional scanning, the projection data was sparsely sub-sampled to 2.5% (24 out of 984) of the views at regular intervals in the range [0°, 180°]. To allow compatibility with the rigid registration method which relies on parallel beam data, needle localization was performed on the same data using parallel beam geometry.
2. A full baseline scan of the phantom without the needle with the full dense sampling of view angles was utilized. Radon-space rigid registration was applied to each pair of baseline/repeat scans using the method described in G. Medan, N. Shamul, L. Joskowicz. "Sparse 3D Radon space rigid registration of CT scans: method and validation study". *IEEE Transactions on Medical Imaging*, accepted October 2016). A measure of registration accuracy was calculated by computing the RMS coordinate error of the rigid registration transformation applied to the phantom voxel coordinates, as compared to the image-space based rigid registration that was used as a substitute for ground truth. Results for global rigid registration error were in the range 0.32-0.75 mm.
3. The needle orientation and marker position for each repeat scan were calculated as described above with reference to FIG. 5—using the needle-less scan as full baseline and with the needle modeled as a single straight segment. FIG. 7 illustrates graphically the resulting orientation, marker position and tip position for each scan.

For comparison, image space needle localization was performed as follows. Since the tip itself is obscured by reconstruction artifacts in the image, it cannot be localized directly in the reconstructed image. Therefore the needle tip was localized indirectly with the following procedure:
1. Localize the marker in image space using its spherical shape in 3D, in a similar fashion to the method used for each circular projection of the marker in 2D projection space.
2. Estimate the 3D orientation of the needle, in a similar fashion to the method used for each projection view of the needle in 2D projection space.
3. Localize the tip by tracing a ray along the calculated needle orientation from the calculated marker position, using the known distance between the marker and the tip.

Figure 8:
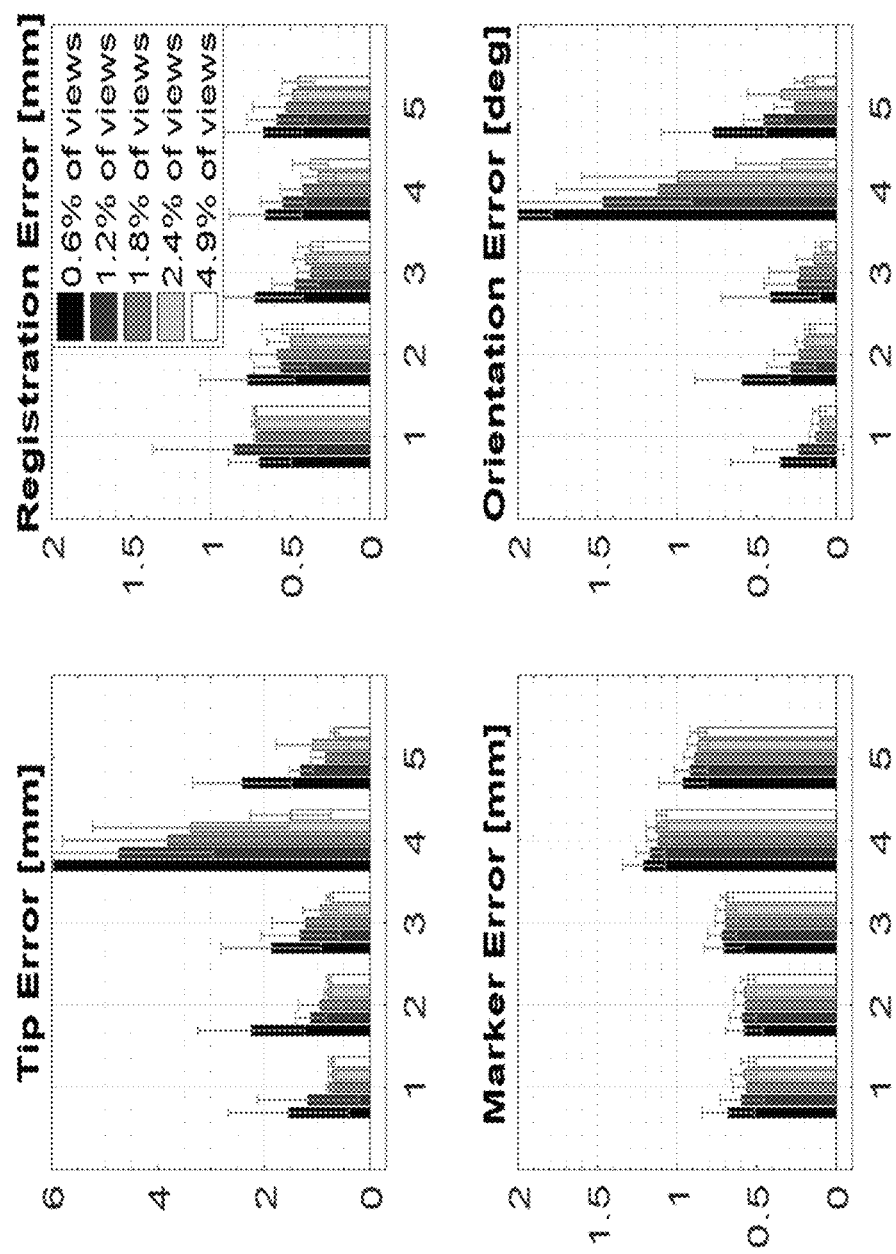
FIG. 8 illustrates the number of projections used as input to the needle localization algorithm and the achieved accuracy.

The tip localization variances for the scans, as well as registration errors, orientation errors and marker localization errors, are shown in FIG. 8 per number of view angles used. The localization in each scan was repeated 45 times to account for randomization due to RANSAC scheme employed in different stages of the calculation and randomized angles selection.

The marker and orientation errors are dependent, which explains why the needle tip localization error may be smaller than the accumulated error resulting from both the marker center localization error and the needle orientation error. As described above, a 2D line was fit through the detected marker center in each projection difference image so that the line coincides with the projection of the needle which appears as a bright thin line. The cost function minimization yields the needle orientation that counteracts the marker localization error because the needle is a line passing through the actual marker center, thereby reducing the cost in the direction that extends back towards the needle.

It is noted that while the presently disclosed projection-space method and the validation image-space method are similar in nature, the latter requires the repeat scan to be fully available in order to reconstruct the image. Consequently it is noted that both methods achieve comparable results, while the projection space method has the potential to significantly reduce the radiation dose required for each localization, compared with its image-space counterpart, via fractional scanning.

Figure 10:
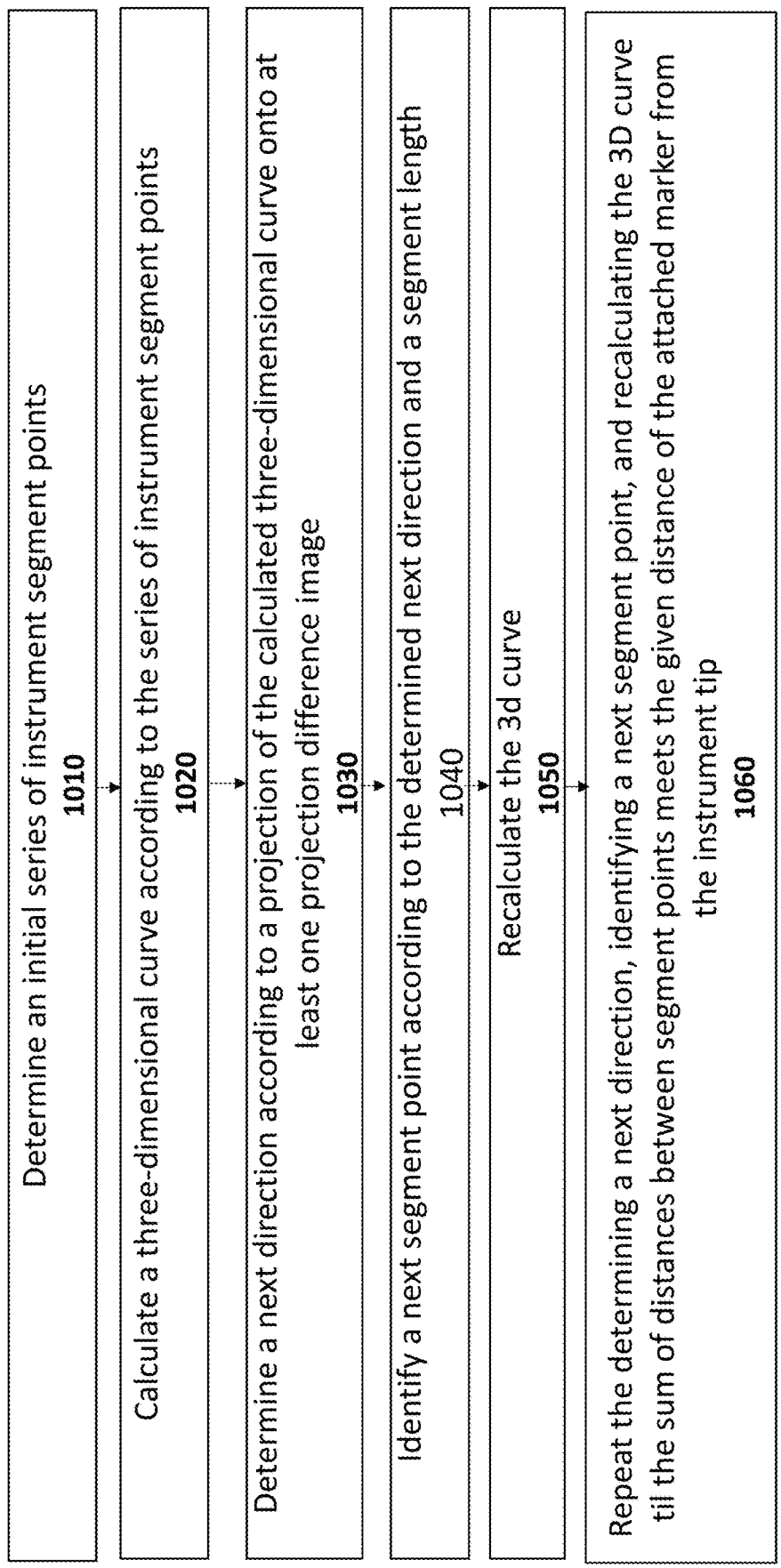
FIG. 10 illustrates an example flow diagram describing a method for locating the tip of a metallic instrument in a case where the instrument is flexible, according to some embodiments of the presently disclosed subject matter.

Attention is now directed to FIG. 10, which illustrates an example flow diagram describing a method for locating the tip of a metallic instrument in a case where the instrument is flexible, according to some embodiments of the presently disclosed subject matter.

In the case of a flexible instrument, the trajectory in 3D space can be estimated by incrementally computing the locations of a series of points (hereforward termed "segment points") along the trajectory of the instrument in 3D space p1, p2, . . . , pi. These segment points can be fitted to a 3D curve (for example: a cubic Bézier curve) Ci that traces the curvilinear shape of the needle from the center of the spherical marker toward the last point pi, where i is the number of segment points. A 3D cubic Bézier curve accurately models needle bending with the typical forces exerted during insertion.

The processing and memory circuit (34) (for example; instrument localization module (342)) can determine (1010) an initial series of instrument segment points. The sequence of segment points can be initialized with—for example— four colinear (for example: colinear and equidistant) points starting from the marker center p1=s with successive points at a distance $\Gamma$ along an initial direction determined by the optimization of a cost function described in the following paragraph. The parameter $\Gamma$ can be a fixed or variable parameter indicating segment length. In some embodiments a minimum of four segment points are required to define the 3D cubic Bézier curve.

This initial direction can, for example, be determined as in the case of a non-flexible metallic instrument as described hereinabove.

The processing and memory circuit (34) (for example; instrument localization module (342)) can calculate (1020) a three-dimensional curve according to the series of instrument segment points. In some embodiments, the three-dimensional curve is a Bezier curve.

A method such as the one described in Khan M (2012) "A new method for video data compression by quadratic Bézier curve fitting" in Signal Image Video Process 6(1):19-24) can be utilized to fit the points to the Bezier curve. The Khan method computes the cubic Bezier curve in 3D space such that the squared sum distance of the segment points from the curve is minimized.

The processing and memory circuit (34) (for example; instrument localization module (342)) can determine (1030) a next direction according to a projection of the calculated three-dimensional curve onto at least one projection difference image.

The next direction can be obtained by optimizing a cost function designed to attain a minimum when the projection of the curve Ci+1 onto the set of projection difference images follows the needle trajectory traced in the images:

$$\Psi_i(\theta, \phi) = -\sum_{j=1}^{K} \left| \int_{r \in c_{i+1}^j [\hat{n}(\theta,\phi)]} Ij(r) dt \right|$$

where $\theta$, $\varphi$ are spherical coordinates, $\hat{n}(\theta, \varphi)$ is the unit vector n expressed in spherical coordinates, and r is the 2D coordinate along the projected trajectory c ji+1[ń] in projection difference image I j. Note that the projection difference image is signed, so pixels with large positive values correspond to coordinates in which the needle is present in the repeat scan but is absent in the baseline. Thus, the needle segment corresponds to a high-intensity section of the difference image.

Thus, the orientation of the ith segment can be $(\theta_i^*, \phi_i^*) = \mathrm{argmin}_{\theta,\phi} \Psi_i(\theta,\phi)$.

The processing and memory circuit (34) (for example; instrument localization module (342)) can identify (1040) a next segment point according to the determined next direction and a segment length, thereby extending the series of segment points.

The processing and memory circuit (34) (for example; instrument localization module (342)) can recalculate (1050) the 3d curve according to the extended series of segment points.

The processing and memory circuit (34) (for example; instrument localization module (342)) can evaluate (1060) whether the sum of distances between segment points meets the given distance of the attached marker from the instrument tip. If not, processing and memory circuit (34) (for example; instrument localization module (342)) can then repeat the determining a next direction, identifying a next segment point, and recalculating the 3D curve. The incremental computation can stop once the length of the 3D curve Ci+1 exceeds the distance between the marker and flexible needle tip. The flexible needle tip position can be determined by trimming the last segment so that the overall length of the curve is equal to the known distance between the marker and the needle tip.

The method of FIG. 10 was tested using an abdomen phantom (CIRS model 57 Triple Modality 3D Abdominal Phantom). Inserted into it were two flexible needles: a long 16-gauge needle (1.65 mm outer diameter) and a short 22-gauge needle (0.72 mm outer diameter). A spherical marker was attached to each needle at a predetermined distance from the tip: For the long needle, the marker center was set at 235 mm from the tip; for the short needle, the distance was set at 135 mm.

The phantom was scanned on a GE Discovery CT750HD scanner and sinogram and image data were obtained. The reconstructed image size is 800×800×144 voxels, with spatial resolution of 0.58×0.58×1.25 mm3. The detector array consisted of 885 elements scanned at 984 views at regular intervals in the range [0°,360°), where four slices were acquired in each full revolution.

The projection data were re-binned from fan beam to parallel rays geometry.

First, a scan of the empty scanner bed was acquired so that its sinogram can be subtracted from the following scans since the scanner bed does not undergo the same rigid movement as the phantom. Then, a full, dense view angles sampling baseline scan of the phantom was acquired without the needle. At each subsequent scan, the needle with the attached spherical marker was inserted at a different location or different depth.

To mimic patient motion, the phantom was rotated by up to 5° about an arbitrary axis and/or translated by up to 50 mm and a full scan was acquired again. Fractional scanning was simulated by using only a small subset of the view angles. The full baseline scan was registered to each sparse scan with the flexible needle inserted using 3D Radon space rigid registration.

The registration accuracy was evaluated as the root-mean-square of differences between the voxels coordinates after rigid registration transformation and by image space registration of the reconstructed images. A sparse set of 24 evenly spaced view angles in the range [0°,180°) was used for 3D Radon space registration and flexible needle trajectory fitting as in the rigid needle experiments. The choice of 24 view angles was selected from experiments with various values since it proved to be a good trade-off between robustness and potential dose reduction. The segment length parameter $\Gamma$ was set to 15 mm. Experiments showed that lower values were not robust to feature noise in the optimization of segments directions, while greater values overshoot the typical bending of the needles in the experiments. The spherical marker center ground truth coordinates were obtained by manual localization on the reconstructed images.

The flexible needle trajectory ground truth was traced in 3D image space by manually placing segment points on a volumetric difference image and then fitting them to a 3D cubic Bézier curve. The flexible needle tip ground truth location was defined as the point on the needle trace found at the known tip-marker distance. The flexible needle trajectory error was evaluated as the root-mean-squared distance of points along the fitted curve to the nearest point on the ground truth Bézier curve.

FIG. 11 summarizes the results of the flexible needle tip localization for seven CT scans: four with the long needle (L1-4) and three with the short needle (S1-3). One of the scans (L3) yields a large tip localization error due to the needle trajectory being very close to in-plane with the axial plane (FIG. 3). In the presently disclosed method, long needle segments that are in-plane can lead to the inaccurate estimation of the trajectory since the projections of these segments appear as horizontal lines in the projection difference images regardless of the orientation within the plane. This means that there is no unique solution to the inverse problem of the path reconstruction from projections in this degenerate case. Thus, in-plane needle insertion should be avoided to enable the recovery of the needle orientation as an intersection of non-parallel planes.

The running time of the implementation is 200-250 s on an Intel i7 CPU running un-optimized Matlab code. To allow the method to be used in a clinical setting, the code should be optimized and parallelized for GPU computations so as to reduce the running time to 2-5 s. The parallelization is achieved in the projection difference computation step by computing the projection difference images in parallel and in the subsequent segment point additions.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the invention may be, at least partly, implemented on a suitably programmed computer. Likewise, the invention contemplates a computer program being readable by a computer for executing the method of the invention. The invention further contemplates a non-transitory computer-readable memory tangibly embodying a program of instructions executable by the computer for executing the method of the invention.

Those skilled in the art will readily appreciate that various modifications and changes can be applied to the embodiments of the invention as hereinbefore described without departing from its scope, defined in and by the appended claims.

The invention claimed is:

1. A computer-implemented method of locating a tip of a metallic instrument inserted in a body, wherein the method utilizes a baseline sinogram derived from a prior computerized tomography (CT) scanning of the body, and wherein the baseline sinogram comprises projections in N exposure directions, the method comprising:
   a) performing, by a computer, three-dimensional Radon space registration of a sparse repeat sinogram to the baseline sinogram, thereby giving rise to registration parameters,
      wherein the sparse repeat sinogram is derived from a repeat CT scanning of the body and comprises projections in n exposure directions, n being substantially less than N, and wherein the repeat CT scanning is provided with the metallic instrument inserted into the body, the metallic instrument having an attached marker located at a known distance from the instrument tip;
   b) subtracting, by the computer, the baseline sinogram from the repeat sinogram in accordance with the registration parameters to obtain projection difference images, wherein each of the projection difference images is associated with an exposure direction of a respective projection in the repeat sinogram; and
   c) using, by the computer, the projection difference images and the known distance of the attached marker from the metallic instrument tip to determine a three-dimensional location of the metallic instrument tip.

2. The method of claim 1, further comprising:
displaying data indicative of the determined three-dimensional location of the instrument tip.

3. The method of claim 1, wherein the determining a three-dimensional location of the metallic instrument tip comprises:
   i. using projection difference images to identify a three-dimensional location of the marker;
   ii. using the identified three-dimensional location of the marker and the projection difference images to identify a trajectory of the metallic instrument; and
   iii. determining the location of the instrument tip in accordance with, at least, the identified three-dimensional location of the marker, identified instrument trajectory and the known distance of the marker from the tip.

4. The method of claim 2 wherein the displaying data indicative of the determined three-dimensional location of the instrument tip comprises displaying a volume reconstruction in accordance with the baseline sinogram.

5. The method of claim 3, wherein the marker is spherical, and wherein the identifying a three-dimensional location of the spherical marker comprises:
   i) identifying, in each of at least two projection difference images, a projection of the spherical marker;
   ii) computing a two-dimensional center coordinate location of at least two identified projections of the marker, and
   iii) calculating a three-dimensional location of the spherical marker according to, at least, at least two computed two-dimensional center coordinate locations.

6. The method of claim 3, wherein the identifying a trajectory of the metallic instrument comprises:
   i) identifying, for at least two projection difference images, a direction maximizing an accumulated intensity along the direction, thereby giving rise to at least two identified projections of the metallic instrument;
   ii) determining at least two instrument projection planes according to, at least:
      a. a line derived from a respective identified projection of the metallic instrument, and
      b. a geometry of a CT scanner, and
   iii) calculating a trajectory of the metallic instrument according to, at least, at least two determined instrument projection planes.

7. The method of claim 5, wherein the identifying a projection of the spherical marker in a projection difference image comprises performing two-dimensional cross-correlation of the projection difference image with a circular pattern.

8. The method of claim 5, wherein the identifying a projection of the spherical marker in a projection difference image comprises processing of the projection difference image by a neural network.

9. The method of claim 5, wherein the calculating a three-dimensional location of the spherical marker comprises:
solving a system of projection matrix equations,
wherein each projection matrix equation comprises a matrix determined according to, at least:
i. a geometry of a CT scanner;
ii. the computed center coordinate location of a projection difference image; and
iii. the exposure direction of the projection difference image.

10. The method of claim 6, wherein the calculating the trajectory of the metallic instrument comprises:
solving a system of equations,
wherein each equation comprises a scalar product of an orientation vector with a normal vector of an instrument projection plane,
thereby giving rise to data informative of the trajectory of the metallic instrument.

11. The method of claim 6, wherein the metallic instrument is flexible, and wherein the calculating the trajectory of the metallic instrument comprises:
i. determining an initial series of instrument segment points;
ii. calculating a three-dimensional curve according to the series of instrument segment points;
iii. determining a next direction according to, at least, a projection of the calculated three-dimensional curve onto at least one projection difference image;
iv. identifying a next segment point according to, at least, the determined next direction and a segment length, thereby extending the series of segment points;
v. recalculating the three-dimensional curve according to the extended series of segment points; and
vi. repeating iii-v until a sum of distances between segment points of the series of segment points meets the known distance of the attached marker from the instrument tip.

12. The method of claim 11, wherein the three-dimensional curve is a Bezier curve.

13. A computer-based volume reconstruction unit configured to operate in conjunction with a CT scanner,
the volume reconstruction unit comprising a processing and memory circuitry, the processing and memory circuitry being configured to perform a method of locating a tip of a metallic instrument inserted in a body, wherein the method utilizes a baseline sinogram derived from a prior computerized tomography (CT) scanning of the body, and wherein the baseline sinogram comprises projections in N exposure directions, the method comprising:
a) performing, by a computer, three-dimensional Radon space registration of a sparse repeat sinogram to the baseline sinogram, thereby giving rise to registration parameters,
wherein the sparse repeat sinogram is derived from a repeat CT scanning of the body and comprises projections in n exposure directions, n being substantially less than N, and wherein the repeat CT scanning is provided with the metallic instrument inserted into the body, the metallic instrument having an attached marker located at a known distance from the instrument tip;
b) subtracting, by the computer, the baseline sinogram from the repeat sinogram in accordance with the registration parameters to obtain projection difference images, wherein each of the projection difference images is associated with an exposure direction of a respective projection in the repeat sinogram; and
c) using, by the computer, the projection difference images and the known distance of the attached marker from the metallic instrument tip to determine a three-dimensional location of the metallic instrument tip.

14. The volume reconstruction unit of claim 13, wherein the method of locating a tip of a metallic instrument further comprises:
displaying data indicative of the determined three-dimensional location of the instrument tip.

15. The volume reconstruction unit of claim 13, wherein the determining a three-dimensional location of the metallic instrument tip comprises:
i. using projection difference images to identify a three-dimensional location of the marker,
ii. using the identified three-dimensional location of the marker and the projection difference images to identify a trajectory of the metallic instrument; and
iii. determining the location of the instrument tip in accordance with, at least, the identified three-dimensional location of the marker, identified instrument trajectory and the known distance of the marker from the tip.

16. The volume reconstruction unit of claim 15, wherein the marker is spherical, and wherein the identifying a three-dimensional location of the spherical marker comprises:
i) identifying, in each of at least two projection difference images, a projection of the spherical marker;
ii) computing a two-dimensional center coordinate location of at least two identified projections of the marker; and
iii) calculating a three-dimensional location of the spherical marker according to, at least, at least two computed two-dimensional center coordinate locations.

17. The volume reconstruction unit of claim 15, wherein the identifying a trajectory of the metallic instrument comprises:
i) identifying, for at least two projection difference images, a direction maximizing an accumulated intensity along the direction, thereby giving rise to at least two identified projections of the metallic instrument;
ii) determining at least two instrument projection planes according to, at least:
a. a line derived from a respective identified projection of the metallic instrument, and
b. a geometry of a CT scanner, and
iii) calculating a trajectory of the metallic instrument according to, at least, at least two determined instrument projection planes.

18. The volume reconstruction unit of claim 17, wherein the calculating the trajectory of the metallic instrument comprises:
solving a system of equations,
wherein each equation comprises a scalar product of an orientation vector with a normal vector of an instrument projection plane,
thereby giving rise to data informative of the trajectory of the metallic instrument.

19. The volume reconstruction unit of claim 17, wherein the metallic instrument is flexible, and wherein the calculating the trajectory of the metallic instrument comprises:

i. determining an initial series of instrument segment points;
ii. calculating a three-dimensional curve according to the series of instrument segment points;
iii. determining a next direction according to, at least, a projection of the calculated three-dimensional curve onto at least one projection difference image;
iv. identifying a next segment point according to, at least, the determined next direction and a segment length, thereby extending the series of segment points;
v. recalculating the three-dimensional curve according to the extended series of segment points; and
vi. repeating iii-v until a sum of distances between segment points of the series of segment points meets the known distance of the attached marker from the instrument tip.

20. A computer program product implemented on a non-transitory computer usable medium having computer readable program code embodied therein to cause the computer to perform a method of locating a tip of a metallic instrument inserted in a body, wherein the method utilizes a baseline sinogram derived from a prior computerized tomography (CT) scanning of the body, and wherein the baseline sinogram comprises projections in N exposure directions, the method comprising:

a) performing, by a computer, three-dimensional Radon space registration of a sparse repeat sinogram to the baseline sinogram, thereby giving rise to registration parameters,
  wherein the sparse repeat sinogram is derived from a repeat CT scanning of the body and comprises projections in n exposure directions, n being substantially less than N, and wherein the repeat CT scanning is provided with the metallic instrument inserted into the body, the metallic instrument having an attached marker located at a known distance from the instrument tip;
b) subtracting, by the computer, the baseline sinogram from the repeat sinogram in accordance with the registration parameters to obtain projection difference images, wherein each of the projection difference images is associated with an exposure direction of a respective projection in the repeat sinogram; and
c) using, by the computer, the projection difference images and the known distance of the attached marker from the metallic instrument tip to determine a three-dimensional location of the metallic instrument tip.

* * * * *